United States Patent [19]

Wilson et al.

[11] Patent Number: 5,498,426
[45] Date of Patent: Mar. 12, 1996

[54] LIQUID ANTACID COMPOSITIONS

[75] Inventors: Robert L. Wilson, Mason; Sara A. Ubelhor; William A. Cruz, both of Cincinnati, all of Ohio

[73] Assignee: The Procter & Gamble Company, Cincinnati, Ohio

[21] Appl. No.: 316,981

[22] Filed: Oct. 3, 1994

[51] Int. Cl.$^6$ .......................... A61K 33/42; A61K 33/10
[52] U.S. Cl. ...................... 424/602; 424/714; 424/717; 424/722
[58] Field of Search ...................... 424/712, 715, 424/722, 602

[56] References Cited

U.S. PATENT DOCUMENTS

| | | | |
|---|---|---|---|
| 3,062,714 | 11/1962 | Pitkin et al. | 167/55 |
| 3,329,564 | 7/1967 | Aguiar et al. | 424/602 |
| 3,579,634 | 5/1971 | Brown | 424/154 |
| 3,621,094 | 1/1971 | Mayron et al. | 424/602 |
| 3,767,794 | 10/1973 | McVean et al. | 424/157 |
| 4,163,777 | 8/1979 | Mitra | 424/21 |
| 4,255,413 | 3/1981 | Rattie et al. | 424/37 |
| 4,367,218 | 1/1983 | Jacobsen | 424/715 |
| 4,396,404 | 8/1983 | Mitra | 424/715 |
| 4,446,135 | 5/1984 | Fountaine | 424/154 |
| 4,486,412 | 12/1984 | Shah et al. | 424/156 |
| 4,533,543 | 8/1985 | Morris et al. | 424/38 |
| 4,656,028 | 4/1987 | Cuca | 424/455 |
| 4,784,851 | 11/1988 | Rohwer | 424/715 |
| 4,786,502 | 11/1988 | Chapura et al. | 424/441 |

FOREIGN PATENT DOCUMENTS

| | | | |
|---|---|---|---|
| 2509611 | 2/1983 | France | 424/602 |
| 588020 | 1/1983 | Japan | 424/602 |

OTHER PUBLICATIONS

"Preservation of Pharmaceuticals", F. J. Bandelin, Drug & Cosmetic Review–1950–1951, pp. 123–127.
"Microbiological Stability of Oral Dosage Forms Problems with Liquid Antacids", P. C. Schmidt, University of Marburg, S.T.P. Pharma 1 (8)720–726 1985.
Gennaro, Remington's Pharmaceutical Sciences, 18th Edition (Mack Publishing Company, 1990), pp. 774–776, 778.

Primary Examiner—Peter F. Kulkosky
Attorney, Agent, or Firm—Douglas C. Mohl; Mary Catherine Poland; Jscobus C. Rasser

[57] ABSTRACT

Liquid antacid compositions for neutralizing stomach acid in humans and other animals comprising: an alkaline earth carbonate salt; and alkali metal phosphate salt; an alkali metal bicarbonate salt; and other excipients.

12 Claims, No Drawings

LIQUID ANTACID COMPOSITIONS

This invention relates to novel liquid antacid compositions for neutralizing stomach acid in humans and other animals. In particular, it relates to highly efficacious antacid compositions containing an alkaline earth carbonate salt which are aesthetically acceptable and microbially stable.

Pharmaceutical compositions may be produced in a variety of dosage forms, depending upon the desired route of administration of the active material. Liquid suspensions are one preferred dosage form for delivery of antacid active materials which neutralize stomach acid. Liquid antacid suspensions can be generally defined as two-phase systems, wherein a finely divided antacid active, in solid form, is suspended in a liquid medium These compositions are alkaline, with typical pH values in the range of 7.5 to 8.5.

A problem faced by such liquid compositions, among others, is that the pH may drift high due to equilibrium being established between the carbonate salt and its environment. This results in such things as color changes if a pH sensitive dye is used and acceleration of base catalyzed degradations. The present inventors have found that the compositions can be stabilized in an effective and convenient manner and be aesthetically pleasing. It is therefore an object of the present invention to provide liquid antacid compositions that are both efficacious and aesthetically pleasing to the consumer. It is also an object of the present invention to provide liquid antacid compositions that are pH stable during the shelf life of the composition.

These and other objects of the present invention will become readily apparent from the detailed description which follows.

All percentages and ratios used herein are by weight, and all measurements are made at 25° C., unless otherwise specified.

SUMMARY OF THE INVENTION

The present invention relates to liquid antacid compositions. These compositions comprise: from about 5% to about 40% of an alkaline earth carbonate salt; from about 0.1% to about 2.0% of an alkali metal phosphate salt and from about 0.05% to about 2.0% of an alkali metal bicarbonate salt.

The present invention compositions additionally relate to a method for neutralizing excess stomach acid. The method comprises orally administering to a human or lower animal in need of such treatment a safe and effective amount of the liquid antacid composition according to the present invention.

DETAILED DESCRIPTION OF THE INVENTION

The present invention relates to liquid antacid compositions. These compositions comprise: an alkaline earth carbonate salt; an alkali metal phosphate salt; and an alkali metal bicarbonate salt and other excipients.

All components of the present compositions must be pharmaceutically-acceptable. As used herein, a "pharmaceutically-acceptable" component is one that is suitable for use with humans and/or other animals without undue adverse side effects (such as toxicity, irritation and allergic response) commensurate with a reasonably benefit/risk ratio. The components for use in the present compositions, and the preferred amounts to be utilized, are described in detail hereinafter.

Alkaline Earth Carbonate Salt

The present compositions of the invention contain a safe and effective amount of alkaline earth carbonate salt, preferably calcium carbonate, as a therapeutically effective antacid active component. Calcium carbonate is effective for neutralizing stomach acid in a human or lower animal. Calcium carbonate typically comprises from about 5% to about 40%, and preferably from about 10% to about 30%, by weight of the present compositions.

Alkali Metal Phosphate Salt

The present invention's compositions also comprise from about 0.1% to about 2.0%, preferably from about 0.20% to about 0.50%, of an alkali metal phosphate salt, preferably sodium or potassium, most preferably potassium phosphate. This acts with the bicarbonate salt to buffer the present compositions. The preferred potassium phosphate is potassium monobasic phosphate. The term "alkali metal phosphate salt" is meant to include the various protonated forms such as the mono, di and tribasic salts.

Alkali Metal Bicarbonate Salt

The compositions of the present invention also contain from about 0.05% to about 2.0%, preferably from about 0.08% to about 0.30% of an alkali metal bicarbonate salt, preferably sodium or potassium, most preferably potassium bicarbonate. This salt acts with the phosphate salt to buffer the present compositions.

Other Excipients

The compositions of the present invention may also contain other excipients that modify the physical characteristics and/or therapeutic effects of the present compositions. The other excipients must not, however, adversely affect the antacid therapeutic efficacy of the carbonate used in the compositions. The compositions typically comprise from about 60% to about 95%, preferably from about 70% to about 90%, of other excipients by weight of the compositions.

The excipients, in addition, optionally but preferably are present in the invention compositions at a level which provide an elevated soluble solids content in the composition to enhance microbial stability. Excipients useful in providing an elevated soluble solids content include, for example, glycerin, sorbitol, propylene glycol, mannitol, glucose, sucrose, dextrose, and mixtures thereof. The elevated soluble solids preferably comprise from about 15% to about 40%, more preferably from about 20% to about 40%, by weight of the composition.

The invention compositions also preferably contain a suspension system comprising one or more compounds which maintain the calcium carbonate in an essentially uniform aqueous suspension at typical conditions of storage and use. Such suspension systems, suspension agents, and methods for their use include those well known in the art. See, for example, M. Pernarowski, "Solutions, Emulsions and Suspensions" *Remington's Pharmaceutical Sciences* (A. Osol, editor, 15th Edition, 1975), incorporated herein by reference. Suspension agents useful in the present compositions include xanthan gum, guar gum, cellulose gums, cellulose gum derivatives, magnesium aluminum silicate, carboxy vinyl polymers such as carbopol, and mixtures thereof. The suspension agents typically comprise from about 0.1% to about 1%, and preferably from about 0.10% to about 0.35%, by weight of the antacid compositions.

The present compositions also may contain a humectant, such as glycerin and sorbitol, which provides a benefit as a mixing aid and helps to modify the Water Activity ("A") of the compositions. Glycerin is preferred and commercially available in food grade quality. Glycerin typically comprises from about 1% to about 15%, and preferably from about 3% to about 10%, by weight of the antacid compositions.

A safe and effective amount of simethicone is also a preferred therapeutically active component in the present antacid compositions. Simethicone is a mixture of dimethyl polysiloxanes and silica gel suitably purified for pharmaceutical use and is therapeutically effective as an antiflatulent. Simethicone is described in more detail in *The Merck Index,* 10th Edition, published by Merck & Co., No. 8374 (1983), incorporated herein by reference in its entirety. The present antacid compositions typically comprise simethicone at a level of from about 0.1% to about 2%, and preferably from about 0.3% to about 2.2%, by weight of the composition.

The present compositions also most preferably comprise one or more sweetening agents. These include materials such as: water-soluble sweetening agents such as monosaccharides, disaccharides, and polysaccharides including, for example, xylose, ribose, glucose, mannose, galactose, fructose, dextrose, sucrose, maltose, such as the soluble saccharin salts, e.g., sodium or calcium saccharin salts, cyclamate salts, acesulfam-K and the like, and the free acid form of saccharin; or dipeptide based sweeteners such as L-aspartyl-L-phenylalanine methyl ester and materials described in U.S. Pat. No. 3,492,131 and the like. In general, the amount of sweetener is primarily a matter of taste preference and will vary with the sweetener selected and with the ingredients in the composition being prepared; except that as noted hereinbefore some of these materials may also be present at an elevated level to provide an elevated soluble solids content in the composition to enhance the microbial stability of the composition.

Preferred in the present compositions is a non-nutritive artificial sweetener such as saccharin, and/or a sugar component such as sucrose. Particularly preferred sweetening agents are sucrose and sorbitol. The present compositions comprise from about 5% to about 40% of one or more sweetening agents, and more preferably from about 10% to about 35% of one or more sweetening agents by weight of the antacid compositions.

Preferred other excipients useful in the invention compositions also include colorants, flavorants, other pharmaceutical actives (including other antacid agents), and/or coolants. Preferred coolants in the antacid compositions are N-ethyl-p-menthane-3-carboxamide (known commercially as "WS-3"), 3-1-menthoxypropane- 1,2-diol (known commercially as "TK-10"), and mixtures thereof. These coolants are described in PCT Patent Application Publication No. WO 92-17164, to Upson et al., published Oct. 15, 1992, TK-10 is also described in U.S. Pat. No. 4,459,425 to Amano et al., issued Jul. 10, 1984; and WS-3 is also described in U.S. Pat. No. 4,136,163 to Watson et al., issued Jan. 23, 1979. The disclosures of all three of these patent publications are incorporated by reference herein in their entirety.

The present compositions typically comprise WS-3 at a level of from about 0.0001% to about 0.05%, and TK-10 at a level of from about 0.0001% to about 0.1% by weight of the composition. Colorants and flavorants preferably comprise from about 0.01% to about 1% by weight of the composition.

The compositions of this invention may also contain during the manufacturing process antiseptic agents useful in this process as sanitization aides, but which degrade shortly after making the compositions. Typically these agents are used at levels to provide at least about 5 ppm of the agent in the composition during the manufacturing process, and preferably at a level of at least 300 ppm. Preferred are hydrogen peroxide, chloramine, and hypochlorite and its salts (e.g., calcium; sodium; potassium). Such materials are described, for example, in *Disinfection, Sterilization and Preservation* 3d (S. Block ed., 1983), incorporated by reference herein.

The present compositions may also comprise benzyl alcohol. Benzyl alcohol is described in more detail in *The Merck Index,* 10th Edition, published by Merck & Co., No. 1130 (1983), incorporated herein by reference in its entirety. The compositions typically comprise benzyl alcohol at a level of from about 0.001% to about 1%, and preferably from about 0.01%, to about 0.5%, by weight of the compositions to act as a preservative.

The present compositions further comprise short chain alkyl esters of p-hydroxybenzoic acid, which are preservatives also known as "parabens", preferably the methyl, propyl, butyl, and ethyl esters of p-hydroxybenzoic acid. These compositions are approved by the Federal Drug Administration as antimicrobial agents for use in foods and pharmaceuticals. Propylparaben, methylparaben, and mixtures thereof are preferred for use in the present antacid compositions. These materials are described in more detail in *The Merck Index,* 10th Edition, published (1983) by Merck & Co.: No. 7767 ("propylparaben"), No. 5977 ("methylparaben"), No. 3781 ("ethylparaben"), and No. 1556 ("butylparaben"), all incorporated herein by reference in their entirety. These materials are preferably used at levels which reduce or eliminate the negative aesthetics of these parabens in the compositions such that the consumer cannot detect their presence in the present antacid compositions.

The invention compositions may comprise short chain alkyl esters of p-hydroxybenzoic acid at a level of from about 0.001% to about 0.5%, preferably propylparaben at a level of from about 0.001% to about 0.1%, and methylparaben at a level of from about 0.001% to about 0.5%, by weight of the compositions.

The present antacid compositions may also contain bis-biguanide compounds or the pharmaceutically acceptable salts thereof, at a level of from about 0% to about 0.2%. Bis-biguanide compounds are described in detail in U.S. Pat. No. 3,934,002, to Haefele, issued Jan. 20, 1976 (incorporated herein by reference in its entirety).

Chlorhexidine and its pharmaceutically acceptable salts are preferred bis-biguanide compounds that are useful in the present compositions. The term "pharmaceutically acceptable salts", as used herein, means salts of the bis-biguanide compounds which have the same general properties as the compounds from which they are derived, and which are acceptable from a toxicity viewpoint. Preferred salts include the acetate, the hydrochloride, and the gluconate salts. The most preferred bis-biguanide compound is chlorhexidine gluconate. Chlorhexidine, and its gluconate salt, are commercially know and described in *The Merck Index,* 10th Edition, published by Merck & Co., No. 2057 (1983), incorporated herein by reference in its entirety. Chlorhexidine may be used in the present antacid compositions at a level of from about 0.0001% to about 0.005%, and preferably from about 0.0001% to about 0.002% by weight of the composition.

Method of Treatment

The present invention compositions additionally relate to a method for neutralizing excess stomach acid. The method of treatment herein comprises orally administering to a human or lower animal in need of such treatment a safe and effective amount of a liquid antacid composition according to the present invention.

The term "safe and effective amount", as used herein, means a quantity of the calcium carbonate-containing liquid antacid composition sufficient to yield the desired antacid efficacy without undue adverse side effects (such as toxicity, irritation or allergic response) commensurate with a reasonable benefit/risk ratio when used in the manner of this invention. The specific safe and effective amount will, obviously, vary with such factors as the particular condition that is being treated, the severity of the condition, the duration of the treatment, the physical condition of the patient, the nature of concurrent therapy (if any), and the specific formulation and optional components employed. However, a patient in need of such treatment will typically receive from about 500 mg to about 8000 mg of calcium carbonate daily.

The following examples further demonstrate and describe embodiments with the scope of the present invention. The examples are given solely for the purpose of illustration and are not to be construed as a limitation of the present invention as many variations thereof are possible without departing from the spirit and scope.

| Components | Weight % |
| --- | --- |
| Calcium Carbonate | 10.83 |
| Simethicone Emulsion (30%) | 1.108 |
| Benzyl Alcohol | 0.20 |
| Methylparaben | 0.05 |
| Propylparaben | 0.01 |
| Hydrogen Peroxide (3% Solution) | 0.60 |
| TK-10[1] | 0.0024 |
| WS-3[2] | 0.0084 |
| Vanilla Creme Flavor | 0.06 |
| Mint Flavor 1183 | 0.0045 |
| Sucrose | 15.0 |
| Sorbitol | 11.0 |
| Green Color | 0.0014 |
| Xanthan Gum | 0.09 |
| Guar Gum | 0.081 |
| Glycerin | 5.0 |
| Potassium Phosphate Monobasic | 0.25 |
| Potassium Bicarbonate | 0.08 |
| Water | 55.6243 |

[1&2]Coolants as described herein.

This composition is prepared by dispersing guar and xanthan gum until a uniform mixture is obtained. The following ingredients are then added slowly with mixing in the order: potassium bicarbonate, calcium carbonate, dye solution (comprising potassium monobasic phosphate and TK-10), sucrose, glycerin, sorbitol, simethicone emulsion preservative mixture, flavor mixture and hydrogen peroxide.

Ingestion by a person in need of antacid treatment of 1 tablespoon of this composition delivers 1950 mg of calcium carbonate effective for neutralizing the stomach acid of the person in need of the treatment.

| Components | Weight % |
| --- | --- |
| Calcium Carbonate | 20.15 |
| Simethicone Emulsion (30%) | 2.067 |
| Benzyl Alcohol | 0.20 |
| Methylparaben | 0.05 |
| Propylparaben | 0.01 |
| Hydrogen Peroxide (3% Solution) | 0.60 |
| TK-10[1] | 0.0024 |
| WS-3[2] | 0.0060 |
| Vanilla Creme Flavor | 0.06 |
| Mint Flavor 1183 | 0.0055 |
| Sucrose | 15.0 |
| Sorbitol | 11.0 |
| Green Color | 0.0014 |
| Xanthan Gum | 0.06 |
| Guar Gum | 0.06 |
| Glycerin | 5.0 |
| Potassium Phosphate Monobasic | 0.45 |
| Potassium Bicarbonate | 0.30 |
| Water | 44.9777 |

[1&2]Coolants as described herein.

Example II is prepared by a method similar to that described in Example I.

Ingestion by a person in need of antacid treatment of 1 tablespoon of this composition delivers 3900 mg of calcium carbonate effective for neutralizing the stomach acid of the person in need of the treatment.

What is claimed is:

1. A liquid antacid composition being pH stable during its shelf life consisting essentially of:
   a) from about 5% to about 40% of an alkaline earth carbonate salt;
   b) from about 0.1% to about 2.0% of an alkali metal phosphate salt;
   c) from about 0.05% to about 2% of an alkali metal bicarbonate salt;
   d) the remainder other excipients.

2. The composition according to claim 1 further comprising simethicone.

3. The composition according to claim 1 wherein the alkaline earth carbonate salt is calcium carbonate.

4. A composition according to claim 3 wherein the phosphate and bicarbonate salts are potassium salts.

5. A liquid antacid composition being pH stable during its shelf life consisting essentially of:
   a) from about 10% to about 30% calcium carbonate;
   b) from about 0.20% to about 0.50% of potassium phosphate; monobasic
   c) from about 0.08% to about 0.30% of potassium bicarbonate;
   d) from about 70% to about 90% other excipients.

6. The composition according to claim 5 wherein the excipients include an agent selected from the group consisting of glycerin, sorbitol, propylene glycol, mannitol, glucose, sucrose, dextrose, and mixtures thereof.

7. The composition according to claim 6 further comprising from about 0.1% to about 2% simethicone.

8. A method for neutralizing excess stomach acid in a human or lower animal, said method comprising orally administering to a human or lower animal in need of such treatment a safe and effective amount of the liquid antacid composition according to claim 1.

9. A method for neutralizing excess stomach acid in a human or lower animal, said method comprising orally administering to a human or lower animal in need of such treatment, a safe and effective amount of the liquid antacid composition according to claim 2.

10. A method for neutralizing excess stomach acid in a human or lower animal, said method comprising orally administering to a human or lower animal in need of such treatment, a safe and effective amount of the liquid antacid composition according to claim 3.

11. A method for neutralizing excess stomach acid in a human or lower animal, said method comprising orally administering to a human or lower animal in need of such treatment, a safe and effective amount of the liquid antacid composition according to claim 4.

12. A method for neutralizing excess stomach acid in a human or lower animal, said method comprising orally administering to a human or lower animal in need of such treatment, a safe and effective amount of the liquid antacid composition according to claim 7.

* * * * *